United States Patent [19]

Pezzi

[11] 4,424,707

[45] Jan. 10, 1984

[54] METHOD AND DEVICE FOR THE ELECTROPNEUMATICAL TESTING OF THE AIR PERMEABILITY OF CIGARETTES

[75] Inventor: Giovanni Pezzi, Bologna, Italy

[73] Assignee: Sasib S.p.A., Bologna, Italy

[21] Appl. No.: 305,852

[22] Filed: Sep. 25, 1981

[30] Foreign Application Priority Data

Oct. 7, 1980 [IT] Italy ................................ 12674 A/80

[51] Int. Cl.³ .......................................... G01N 15/00
[52] U.S. Cl. ...................................................... 73/38
[58] Field of Search ........................................... 73/38

[56] References Cited

U.S. PATENT DOCUMENTS 3,258,117 6/1966 Domeck, Jr. et al. .
3,408,858 11/1968 Kaeding et al. .
3,412,856 11/1968 Esenwein .
3,690,149 9/1972 Pezzi .
3,962,906 6/1976 Heitmann et al. .
3,991,605 11/1976 Reuland .
4,103,535 8/1978 Mutter et al. .
4,127,025 11/1978 Mills et al. .
4,154,090 5/1979 Heitmann et al. .
4,223,551 9/1980 Greve et al. .
4,227,397 10/1980 Neri .

Primary Examiner—S. Clement Swisher
Assistant Examiner—Joseph W. Roskos
Attorney, Agent, or Firm—Spencer & Frank

[57] ABSTRACT

A device for the electropneumatical testing of the air permeability wherein each cigarette is subjected to at least one test consisting of applying pneumatic pressure to one end of the cigarette and determining the resistance or the pressure drop at the input to the cigarette. The measured pneumatic pressure is transformed into electric measurement signals which are compared with electric reference or threshold signals. According to the invention, the electric measurement signals are compared with the electric reference signals which are shaped as saw-tooth signals and are generated in synchronism with the cigarette tests, that is with the measurement signals. The ascending portions of the sawtooth reference signals have a rate of increasing magnitude which corresponds approximately to the rate of increase of the electric measurement signals.

7 Claims, 3 Drawing Figures

METHOD AND DEVICE FOR THE ELECTROPNEUMATICAL TESTING OF THE AIR PERMEABILITY OF CIGARETTES

BACKGROUND AND SUMMARY OF THE INVENTION

The present invention relates to a method and device for electropneumatically testing the permeability in the longitudinal and/or transverse direction of cigarettes, including filter cigarettes and ventilated cigarettes, by subjecting each cigarette to at least one testing operation which consists of applying a pneumatic pressure to a part of the cigarette, for example to one end and/or to a portion of the wrapper, in determining the resistance or pressure drop at the input of the cigarette, transforming same into an electric measurement signal, and finally comparing said measurement signal with at least one electric reference or threshold signal.

Methods and devices of the above referred type are known, for example, from U.S. Pat. Nos. 3,690,149 and 4,227,397 and from my pending U.S. application Ser. No. 228,882 filed on Jan. 22, 1981.

It is known that in the methods and devices of known type, the value of the electric measurement signal corresponding to the pneumatic pressure which is measured, increases progressively in time until it reaches a maximum value which is substantially constant.

It is known, moreover, that upon increase of the speed of production of the cigarette-making machine which supplies the cigarettes to be tested, there is a corresponding increase of the speed of passage of the cigarettes through the device for electropneumatically testing their permeability. Consequently, the time allowed for each testing operation of each single cigarette is reduced, and also the value of the pneumatic pressure and of the corresponding electric measurement signal is reduced accordingly. As a consequence it happens that, if the electric reference or threshold signal presents a constant value, as in the known type devices, a cigarette which is considered as acceptable at a certain speed of production of the cigarette-making machine, can be rejected as not acceptable at a higher speed, or a cigarette which is considered not acceptable at a certain speed of the cigarette-making machine can become acceptable at a lower speed.

In order to obviate the above inconvenience, it has been proposed to modify the level of the electric reference signal, or the amplification (gain) of the amplifier for the measurement signals, as a function of the actual feeding speed of the cigarettes to be tested. These remedies, although successful, present the inconvenience of a construction which is rather complicated and costly, such as for example the need to utilize non-linear amplifiers, the design and the calibration of which are rather difficult whenever it is required to guarantee a constant measurement at all speeds.

The present invention has for its object to eliminate the above mentioned inconveniences and to provide, with the aid of simple components which can be easily calibrated, very precise testing of the permeability of cigarettes, at all speeds between zero speed and the maximum speed production and of feeding of the cigarettes.

According to the invention, the electric measurement signals are compared with electric reference or threshold signals which are shaped as saw-tooth signals, and are generated in synchronism with the tests of the cigarettes and consequently in synchronism with the electric measurement signals, the ascending portions of said reference signals having a rate of increase which corresponds approximately to the rate of increase of the electric measurement signals. That is, the increasing portions of the reference and measuring signals have the same approximate shape. In this case, therefore, the evaluation of the quality of the cigarette based upon the comparison between the measurement signal and the simultaneous saw-tooth reference signal is absolutely independent of the speed feeding of the cigarettes to be tested and their passage through the testing device, since both the measurement signal and the reference signal increase at least approximately at the same rate during the testing time of each cigarette.

The saw-tooth reference signals can be generated and synchronized with the measurement signals by means of any suitable devices. The invention however provides for a preferred device, in which the saw-tooth reference signals are generated with the aid of a condenser controlled by a charge switch and a discharge switch, said switches being operated by electrical pulses generated in synchronism with the rate of passage of the single cigarettes through the testing device.

The above and other features of the invention, and the advantages deriving therefrom, will appear evident from the following description of a preferred embodiment thereof, made by way of non-limiting example by making reference to the attached sheet of drawings.

DESCRIPTION OF THE PREFERRED EMBODIMENT

Figure 1:
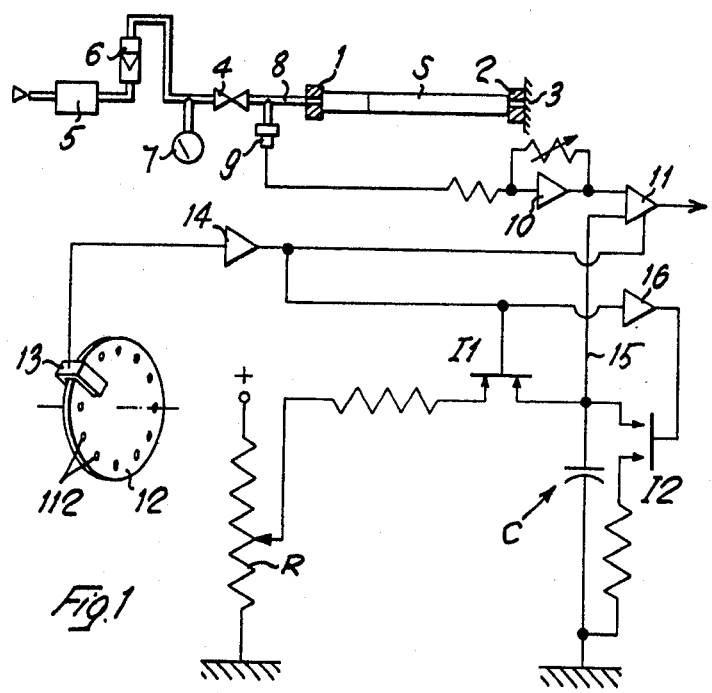
FIG. 1 shows a simplified diagram of the device according to the invention.

In the drawings, reference letter S indicates a cigarette which is to be tested to determine its longitudinal and/or transverse permeability. For this purpose, the cigarette S may be subjected to one single test or to two or more subsequent tests. Each one of said tests consists, for example, of applying a pneumatic test pressure by means of a mouthpiece 1 at one end of the cigarette S, while the other end of the cigarette is maintained open or (as shown in FIG. 1) tightly sealed, for example by means of another mouthpiece 2 which presents a passage closed by a suitable closure member 3.

In the embodiment shown in FIG. 1, the pneumatic test pressure is applied to the mouthpiece 1 (which presents a suitable passage) and consequently to the respective end of the cigarette S by means of a pressure reducing valve 4, which constitutes a known reference pneumatic resistance fed by a pneumatic pressure feeder-stabilizer 5 and a flowmeter 6. The pressure value upstream of the reducing valve 4 may be read by means of a pressure meter 7, branched off the conduit connecting the reducing valve 4 and the pneumatic pressure feeder-stabilizer 5. From the conduit 8 which connects the pressure reducing valve 4 and the mouthpiece 1 there is branched off a pressure transducer 9 which measures the pressure inside the cigarette S during a predetermined test period and transforms said pressure into a corresponding electric measurement signal SM.

The cigarettes S coming, for example, from a cigarette-making machine may be subjected to the above mentioned test end, if desired or required, to one or more subsequent similar tests, by employing any suitable mechanical device. Suitable devices are described, for example, in the U.S. Pat. No. 3,690,149 and in my pending U.S. application Ser. No. 228,882 filed on Jan. 22, 1981.

Figure 3:
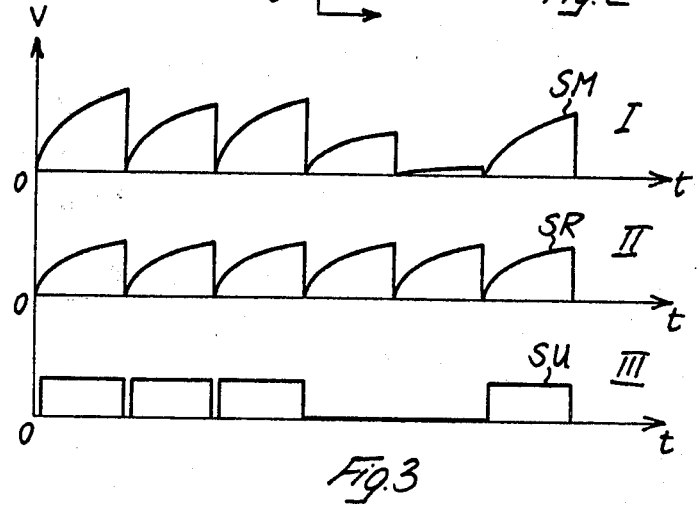
FIG. 3 illustrates some electric signals obtained by employing the device according to FIG. 1.

A sequence of some electric measurement signals SM obtained at the output of transducer 9 are illustrated in diagram I of FIG. 3.

In the embodiment according to FIG. 1, in which the pressure reducing valve 4 constitutes a pneumatic resistance of the same order of magnitude as the pneumatic resistance of the cigarette, the pneumatic pressure inside the tested cigarette S increases in time according to an exponential law, or the like. Consequently, also the corresponding electric measurement signal SM increases according to an exponential curve, or the like, as shown in the diagram I of FIG. 3. In other words, the electric measurement signals SM at the output of transducer 9 consist of saw-tooth signals the ascending section of each of which presents a curved-convex exponential or the like shape, and which follow one another at a rate corresponding to the rate of testing of the subsequent cigarettes S fed to the testing device. The duration of each single electric measurement signal SM, that is the length of the respective saw-tooth signal, corresponds to the test time for each cigarette.

In the embodiment shown in FIG. 1, there is tested the permeability in the transverse direction of the cigarette S, that is the permeability of the wrapper of the cigarette S itself. The terminal values of the electric measurement signals SM correspond to the pressure reached inside the single cigarettes and are therefore inversely proportional to the tested permeability. Thus, for example, in diagram I of FIG. 3 the first three electric measurement signals SM and the sixth electric measurement signal SM correspond to a high pneumatic pressure reached inside the cigarette S at the end of the test period, and indicate therefore a low permeability of the wrapper of the tested cigarettes. The fourth electric measurement signal SM of diagram I corresponds to a medium pneumatic pressure reached inside the cigarette S and therefore to a medium permeability of the cigarette wrapper, while the fifth signal SM of the said diagram I indicates a low pressure reached inside the cigarette and consequently a high permeability of the wrapper.

As previously mentioned, the cigarette S may be subjected to any other suitable pneumatic tests: more particularly, the pneumatic pressure can be applied at the mouthpiece 1 by keeping open the opposite mouthpiece 3, or alternately by applying the pneumatic pressure at the mouthpiece 3 by keeping closed or open the opposite mouthpiece 1. The pneumatic pressure can be applied to at least one end of the cigarette, while covering at least one portion of the side surface of the cigarette. Finally, it is possible to apply the pneumatic pressure to at least one portion of the side surface of the cigarette while keeping closed or open one or both ends of the cigarette.

Each cigarette S may be subjected to one single or to two or more tests of the above mentioned type, preferably at respective subsequent testing stations. For each type of test there will be provided a pressure transducer 9 which transforms into an electric measurement signal the pneumatic pressure taken during the test.

The electric measurement signal SM supplied by the transducer 9 is applied, by means of an amplifier 10, to a comparator 11 which can be permanently inserted or, as in the present case, is intermittently inserted at the end of the test period of each cigarette, by means of electric synchronization signals corresponding to the rate of flow of the cigarettes through the testing station. In the illustrated embodiment, the said synchronization signals are obtained by means of a sychronization disc 12 which rotates synchronously with the speed of feeding of the cigarettes S to the testing station, and which presents a crown of through openings 112. Astride the peripheral portion provided with the openings 112 of the said disc 12 there is provided a fixed U-shaped element 13, one leg of which carries a source of light and the other leg a photocell. The light passing through the openings 112 of the rotating disc 12 generates in the photocell a sequence of electric synchronization signals which are applied, by means of a Schmitt Trigger circuit 14, to the comparator 11, so as to insert same in synchronism with the movement of the cigarettes S through the testing station.

The electric measurement signals SM are compared in the comparator 11 with electric reference or threshold signals SR consisting of saw-tooth signals generated in synchronism with the rate of passage of the cigarettes S through the testing station and consequently in synchronism with the said electric measurement signals SM. A sequence of electric reference or threshold saw-tooth signals SR, applied to the comparator 11, are illustrated in diagram II of FIG. 3. It appears evident that, besides having the same duration as the respective electric measurement signals SM and besides being perfectly synchronized with these measurement signals, the ascending portion of the electric reference signals SR presents a curved-convex shape which corresponds at least approximately to the exponential law (or the like) by which the electric measurement signal SM, corresponding to the pneumatic pressure inside the cigarette, increases.

In the embodiment shown in FIGS. 1 and 3, the electric reference signals SR are generated with the aid of a voltage generator and of a condenser C. This embodiment of the present invention is based on the consideration that, in the realization of the device according to FIG. 1 (in which the cigarette S is connected to the pneumatic pressure generator 5 through a pneumatic resistance 4 of the same order of magnitude as the pneumatic resistance of the cigarette) the rate of increase of the electric measurement signal SM is similar to the rate of charge of a condenser C, due to an electric voltage being impressed thereacross. Consequently, the condenser C, coonnected by means of a conductor 15 to comparator 11, is inserted in the circuit of an electric voltage in series with a resistor R and with a charge switch I1, and is shunted by means of a discharge switch I2. The resistor R can be adjusted at will in order to modify the level of the electric reference or threshold signals SR. The two switches I1, I2 can be of any type (analogical, mechanical or electronic) and are controlled by the electric synchronization signals generated at the rate of passage of the cigarettes S through the testing station, that is by the photocell associated with the rotating disc 12 and by the Schmitt Trigger circuit 14. The control of the two switches I1, I2 takes place in such a manner (for example with the aid of an inverter 16) that the charge switch I1 remains closed and the discharge switch I2 remains open from the starting of the testing of a cigarette S up to the end of the said testing, at which moment the discharge switch I2 is closed and the charge switch I1 is opened, for a very short time.

The comparison of the electric measurement signals SM with the electric reference or threshold signals SR in the comparator 11 furnishes the output signals SU which are illustrated in the diagram III of FIG. 3. It appears evident that for the cigarettes, for which the final value of the electric measurement signals SM is not lower than the corresponding value of the electric reference signal SR, at the output of comparator 11 there is obtained a determined constant signal SU as illustrated for the first, second, third, and sixth testing operation in the diagram III of FIG. 3. On the contrary, there is not obtained any signal SU at the output of comparator 11 whenever the final value of the electric measurement signal SM is lower than the corresponding value of the electric reference signal SR.

The electric signals SU obtained at the output of the comparator 11 can be utilized in any manner in order to evaluate the quality of the cigarette being tested and, for example, in order to accept or to reject the said cigarette, with the aid of any suitable devices of known type.

From the above it appears evident that the device according to the invention guarantees the precision of testing at any rate of speed feeding of the cigarettes and consequently at all speeds of production of the cigarette-making machine. In fact, upon variation of said speeds, there corresponds also the variation of the testing rate of the cigarettes and consequently the testing time period for each single cigarette, but the electric measurement signal SM corresponding to the pressure reached in the cigarette at the end of the testing period, although it varies in relation to the actual testing time, is always compared with an equivalent electric reference or threshold signal SR, since said last signal also varies substantially and at least approximately according to the same law in relation with the testing time period.

Figure 2:
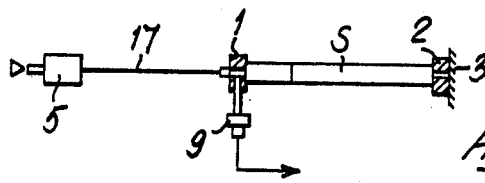
FIG. 2 shows a detail of a modified embodiment of the device according to FIG. 1.

The electric measurement signals SM and consequently the corresponding electric reference signals SR can increase in time according to any other law different from the exponential law and therefore their ascending portion may present any other shape, for example curved-concave or rectilinear. This latter case of signals presenting a rectilinear ascending portion is obtained, for example, by connecting the cigarette S to the pneumatic feeder 5 through a generator of pneumatic current, consisting for example of a capillary duct 17 which determines a pneumatic resistance having an order of magnitude much higher, and for example 100 times higher, than the pneumatic resistance S of the cigarette S itself, as shown in the embodiment according to FIG. 2. In order to obtain corresponding electric reference saw-tooth signals Sr having a rectilinear ascending portion, the same device as shown in FIG. 1 can be utilized, by substituting the voltage generator with an electric current generator.

The embodiment shown in FIGS. 1 and 3 relates to the comparison of the electric measurement signals SM with electric reference signals SR relating to a lower threshold. The invention can be applied also to the comparison of the electric measurement signals with electric reference saw-tooth signals relating to an upper threshold, or to the simultaneous comparison of the electric measurement signals with electric reference signals relating to two or more thresholds.

It is believed that the invention will have been clearly understood from the foregoing detailed description of a preferred embodiment. Changes in the details of construction may be restorted to without departing from the spirit of the invention, and it is accordingly intended that no limitation can be implied and that the hereto annexed claims be given the broadest interpretation to which the employed language fairly admits.

I claim:

1. The method of electropneumatically testing cigarettes to determine whether the air permeability thereof is acceptable, comprising the steps of:

applying a pneumatic pressure to said cigarettes;

measuring the pressure within each of said cigarettes during application of said pneumatic pressure thereto;

transforming said pressure measurement into an electric measurement signal, said electric measurement signal having a saw-tooth shape with an ascending portion which reaches a maximum value followed by a rapidly descending portion, the ascending portion of said measurement signal increasing at a predetermined rate when pressure is applied to a cigarette having an acceptable air permeability;

generating an electric reference signal having a saw-tooth shape in synchronism with said electric measurement signal, the ascending portion of said reference signal increasing at approximately said predetermined rate; and comparing said measurement and reference signals in a comparator, the output of said comparator having a first value indicating that the cigarette is acceptable when the maximum value of said measurement signal is not less than the corresponding value of said reference signal, and a second value indicating that the cigarette is rejected when the maximum value of said measurement signal is less than the corresponding value of said reference signal.

2. The method according to claim 1 wherein the rate at which the ascending portion of said measurement signal increases is exponential, and wherein said saw-tooth shaped reference signal is generated by charging and discharging an electric condenser in synchronism with said measurement signal.

3. A device for electropneumatically testing cigarettes to determine whether the air permeability thereof is acceptable, comprising means for applying a pneumatic pressure to said cigarettes;

means for measuring the pressure within each of said cigarette during application of said pneumatic pressure thereto;

means for transforming said pressure measurement into an electric measurement signal, said electric measurement signal having a saw-tooth shape with an ascending portion which reaches a maximum value followed by a rapidly descending portion, the ascending portion of said measurement signal increasing at a predetermined rate when pressure is applied to a cigarette having an acceptable permeability;

means for generating an electric reference signal having a saw-tooth shape in synchronism with said measurement signal, the ascending portion of said reference signal increasing at approximately said predetermined rate; and a comparator for comparing said measurement and reference signals, the output of said comparator having a first value indicating that the cigarette is acceptable when the maximum value of said measurement signal is not less than the corresponding value of said reference signal, and a second value indicating that the cigarette is rejected when the maximum value of said measurement signal is less than the corresponding value of said reference signal.

4. A device according to claim 3 wherein said means for generating said reference signal comprises a condenser, and which further comprises means for connecting said condenser to a source of electric energy in synchronism with the generation of said electric measurement signal.

5. A device according to claim 4 wherein said means for connecting said condenser to said source of electric energy comprises a charge switch in series with said condenser and energy source, said device further comprising a discharge switch connected in parallel with said condenser, said charge switch being closed and said discharge switch open during the ascending portion of the saw-tooth shaped measurement signal, and said charge switch being open and said discharge switch being closed during the descending portion of the saw-tooth shaped measurement signal.

6. A device according to claim 4 or 5 which further comprises a pneumatic resistance coupled between said means for applying pneumatic pressure and said cigarette, said pneumatic resistance having a value which is of substantially the same order of magnitude as the pneumatic resistance of said cigarette, and wherein said source of electric energy is a voltage generator.

7. A device according to claim 4 or 5 which further comprises a pneumatic resistance coupled between said means for applying pneumatic pressure and said cigarette, said pneumatic resistance having a value which is of a substantially higher order of magnitude than the pneumatic resistance of said cigarette, and wherein said source of electric energy is an electric current generator.

* * * * *